(12) United States Patent
Klug et al.

(10) Patent No.: US 8,556,848 B2
(45) Date of Patent: Oct. 15, 2013

(54) VALVE FOR MIXING OF SUBSTANCES

(75) Inventors: Richard J. Klug, Roxboro, NC (US); M. Ishaq Haider, Cary, NC (US); Frank Martin, Durham, NC (US)

(73) Assignee: Becton, Dickinson & Company, Franklin Lakes, NJ (US)

( * ) Notice: Subject to any disclaimer, the term of this patent is extended or adjusted under 35 U.S.C. 154(b) by 251 days.

(21) Appl. No.: 12/863,456

(22) PCT Filed: Jan. 12, 2009

(86) PCT No.: PCT/US2009/030700
§ 371 (c)(1),
(2), (4) Date: Jul. 19, 2010

(87) PCT Pub. No.: WO2009/091683
PCT Pub. Date: Jul. 23, 2009

(65) Prior Publication Data
US 2010/0286605 A1 Nov. 11, 2010

Related U.S. Application Data

(60) Provisional application No. 61/011,408, filed on Jan. 17, 2008.

(51) Int. Cl.
*A61M 37/00* (2006.01)
(52) U.S. Cl.
USPC .......................................................... 604/89
(58) Field of Classification Search
USPC .................................................... 604/82–92
See application file for complete search history.

(56) References Cited

U.S. PATENT DOCUMENTS

| | | | |
|---|---|---|---|
| 2,841,145 A * | 7/1958 | Epps | 604/89 |
| 5,630,800 A * | 5/1997 | Blank et al. | 604/82 |
| 5,971,953 A | 10/1999 | Bachynsky | |
| 6,634,872 B1 | 10/2003 | Bougamont et al. | |
| 6,789,313 B2 | 9/2004 | Hendricks | |
| 2007/0078475 A1 | 4/2007 | Bodduluri et al. | |
| 2007/0083162 A1 | 4/2007 | O'Reagan et al. | |

FOREIGN PATENT DOCUMENTS

EP 0112574 A1 7/1984

* cited by examiner

*Primary Examiner* — Theodore J Stigell
*Assistant Examiner* — Melissa A Snyder
(74) *Attorney, Agent, or Firm* — Hoffmann & Baron LLP

(57) ABSTRACT

A valve is provided herein for permitting mixing of at least two components, the valve including a body configured for slidable liquid tight engagement with an injector or drug cartridge barrel. The body includes a proximal end, a distal end, and a channel extending therebetween, the channel having a proximal portion and a distal portion. A poppet is sealingly and slidably disposed in the channel to selectively move between first and second positions. The poppet includes a proximal end, a distal end, and a fluid channel, the fluid channel being defined in the poppet and extending from an outlet opening located distally of the distal end of the body. With the poppet being in the first position, the poppet defines a liquid tight seal in the channel such that liquid flow through the channel is prevented. With the poppet being in the second position, the fluid channel is in communication with the proximal portion of the channel so as to define a liquid flow path from the proximal portion of the channel to the outlet opening. Advantageously, with the subject invention, a valve is provided which permits controlled separation and mixing of substances in a standard injector or drug cartridge barrel, without any modification required thereto.

13 Claims, 3 Drawing Sheets

VALVE FOR MIXING OF SUBSTANCES

FIELD OF THE INVENTION

This invention relates to valves for mixing of at least two substances in a medical injector or drug cartridge.

BACKGROUND OF THE INVENTION

Certain drugs or medicaments (those terms being used interchangeably herein) are preferably provided in powder or dry form (such as a lyophilized form), and require reconstitution prior to administration. Lyophilized drugs, for example, typically are supplied in a freeze-dried form that needs to be mixed with a diluent to reconstitute the substance into a form that is suitable for injection. Medicaments may also be provided in other dry or powder form that require reconstitution.

In addition, drugs may be provided as multipart systems which require mixing prior to administration. For example, one or more liquid (e.g., flowable (slurry or liquid)) components, and/or dry (e.g., powdered or granular) components may be provided in a drug container or delivery device which require mixing prior to administration. The components can be mixed and used to form various administratable drugs, such as insulin.

Prior art devices have been developed that provide a wet component (e.g., liquid) and a dry component (e.g., powder) in separate chambers of a common container with the container being configured to permit the flow of the wet component to the dry component to cause mixing thereof in preparing an administratable solution for injection. U.S. Pat. No. 4,874,381 to Vetter is directed to an injector having a barrel configured for mixing, while U.S. Pat. No. 4,968,299 to Ahlstrand et al. is directed to a drug cartridge having a barrel configured for mixing. Both Vetter et al. and Ahlstrand et al. disclose typical configurations for mixing where a bypass channel is formed in the barrel of the device. As such, the device must be specifically configured for mixing.

SUMMARY OF THE INVENTION

A valve is provided herein for permitting mixing of at least two components, the valve including a body configured for slidable liquid tight engagement with an injector or drug cartridge barrel. The body includes a proximal end, a distal end, and a channel extending therebetween, the channel having a proximal portion and a distal portion. A poppet is sealingly and slidably disposed in the channel to selectively move between first and second positions. The poppet includes a proximal end, a distal end, and a fluid channel, the fluid channel being defined in the poppet and extending from an outlet opening located distally of the distal end of the body. With the poppet being in the first position, the poppet defines a liquid tight seal in the channel such that liquid flow through the channel is prevented. With the poppet being in the second position, the fluid channel is in communication with the proximal portion of the channel so as to define a liquid flow path from the proximal portion of the channel to the outlet opening. Advantageously, with the subject invention, a valve is provided which permits controlled separation and mixing of substances in a standard injector or drug cartridge barrel, without any modification required thereto.

These and other features of the invention will be better understood through a study of the following detailed description and accompanying drawings.

DETAILED DESCRIPTION OF THE INVENTION

With reference to the figures, a valve 10 is shown for permitting mixing of at least two components. As further discussed below, the valve 10 is particularly well-suited for use with reconstitution of one or more drugs where one component is a wet (e.g., liquid) component suitable for reconstituting a dry (e.g., lyophilized powder) component. The valve 10 may be used in a barrel of an injector (i.e., a medical injector), such as a syringe or pen injector, or in the barrel of a drug cartridge. As will be recognized by those skilled in the art, the valve 10 may be used to permit mixing of various components, such as one or more wet components, which may be in any flowable form, such as in a liquid, syrup, or slurry form, and/or one or more dry components, which may be in powder or granular form.

Figure 6:
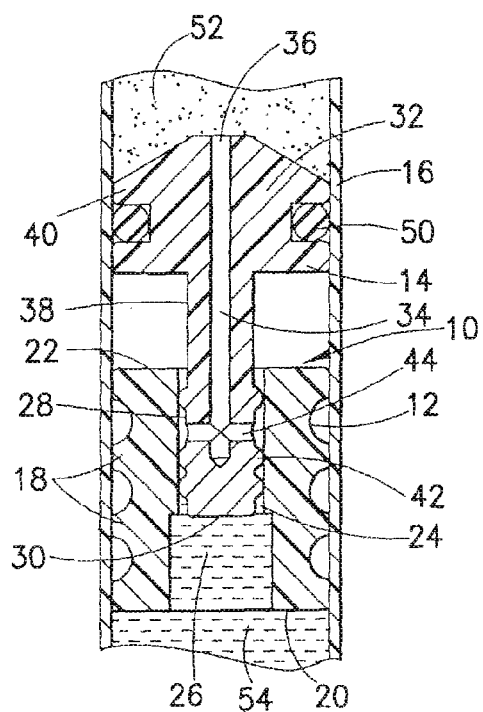
FIG. 6 is a cross-section of the valve of the subject invention in a closed position.
Figure 7:
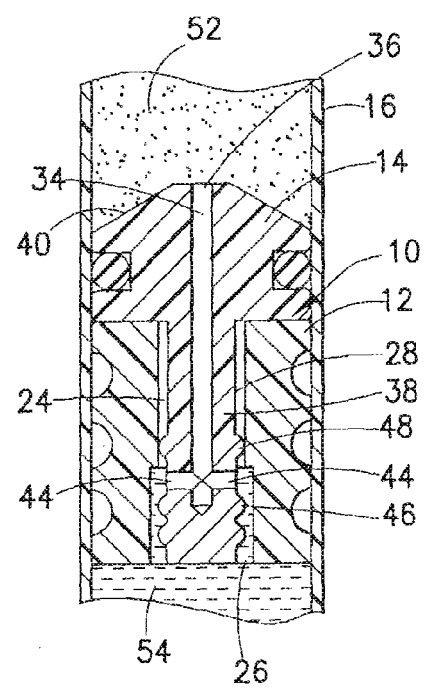
FIG. 7 is a cross-section of the valve of the subject invention in an open position.

The valve 10 generally includes a body 12 and a poppet 14. With reference to FIGS. 6 and 7, the body 12 is configured to be in sliding liquid tight engagement with a surrounding barrel 16. The barrel 16 may be the barrel of an injector or a drug cartridge. The body 12 may be formed of an elastomeric material, particularly any material used in the formation of stoppers or plungers in the injector or drug cartridge art. One or more ribs 18 may be formed about the body 12 to enhance the integrity of the liquid tight seal formed between the body 12 and the barrel 16.

Figure 2:
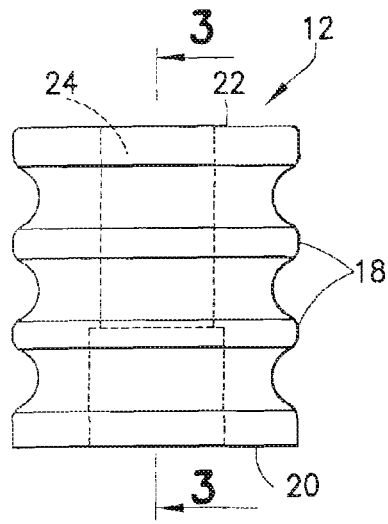
FIG. 2 is a plan view of a body usable with the valve of the subject invention.
Figure 3:
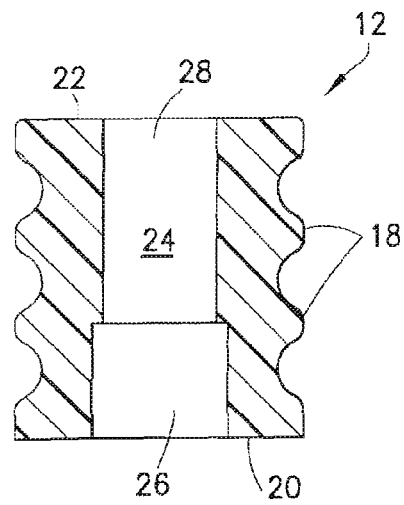
FIG. 3 is a cross-sectional view taken along line 3-3 of FIG. 2.

With reference to FIGS. 2 and 3, the body 12 includes a proximal end 20, which faces away from the patient end of the barrel 16, a distal end 22, which faces the patient end of the barrel 16, and a channel 24 extending therebetween. The channel 24 includes a proximal portion 26, located adjacent to proximal end 20, and a distal portion 28 located adjacent the distal end 22. Preferably, the proximal portion 26 is formed with a larger diameter than the distal portion 28.

Figure 4:
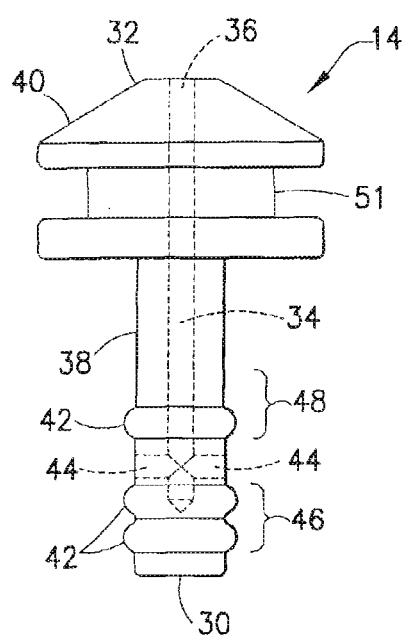
FIGS. 4 and 5 are front and side views of a poppet useable with the valve of the subject invention.
Figure 5:
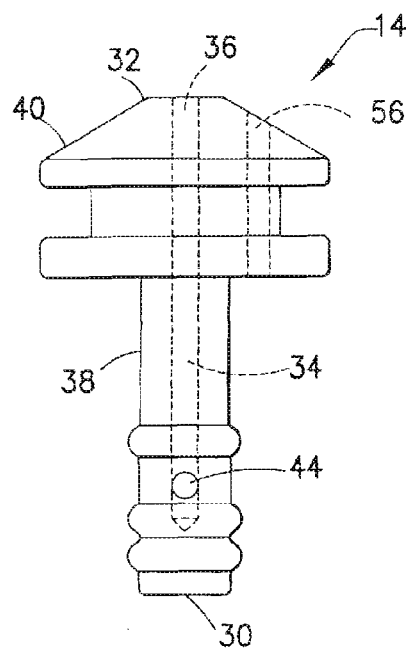

The poppet 14 may be formed of various materials, including being formed of a rigid plastic, such as by injection molding. The poppet 14 is sealingly and slidably disposed in the channel 24 to selectively move between a first position (FIG. 6) and a second position (FIG. 7). As best shown in FIGS. 4 and 5, the poppet 14 includes a proximal end 30, a distal end 32, and a fluid channel 34. The fluid channel 34 is defined in the poppet 14 and extends from an outlet opening 36 that is located distally of the distal end 22 of the body 12.

Although the poppet 14 may be formed with various configurations, preferably, the poppet 14 includes a stem 38 and a head 40. The proximal end 30 is preferably defined on the stem 38 while the distal end 32 of the poppet 14 is defined on the head 40. As shown in FIGS. 6 and 7, the poppet 14 is disposed in the body 12 so as to define a liquid tight seal with the channel 24, preferably at an interface between the stem 38 and the channel 24, more preferably at the interface between the stem 38 and the distal portion 28 of the channel 24. To enhance the integrity of the seal defined between the stem 38 and the channel 34, one or more sealing ribs 42 may be defined on the stem 38.

It is preferred that the fluid channel 34 extend from the outlet opening 36 to at least one inlet opening 44 defined on the stem 38. As shown in FIGS. 4, 6 and 7, two or more of the inlet openings 44 may be provided. It is preferred that the fluid channel 34 have a constant diameter from the outlet opening 36. It is further preferred that the area encompassed by the outlet opening 36 be greater than the collective area(s) of the one or more of the inlet openings 44. In this manner, the outlet opening 36 does not provide a restriction against liquid flowing from the inlet openings 44 and through the fluid channel 34. It is preferred that the inlet openings 44 be spaced from the proximal end 30 of the poppet 14.

Figure 9:
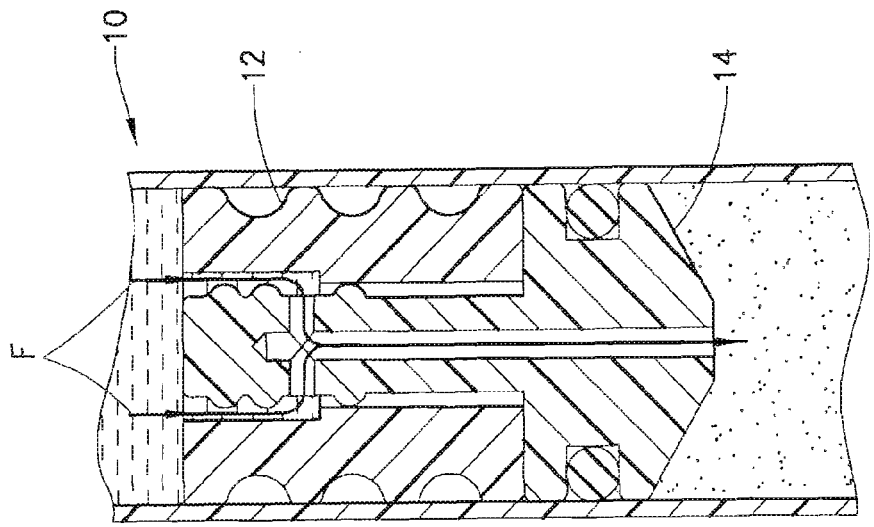
FIGS. 8 and 9 show the valve of the subject invention in closed and open positions, respectively, with fluid flow being shown.
Figure 8:
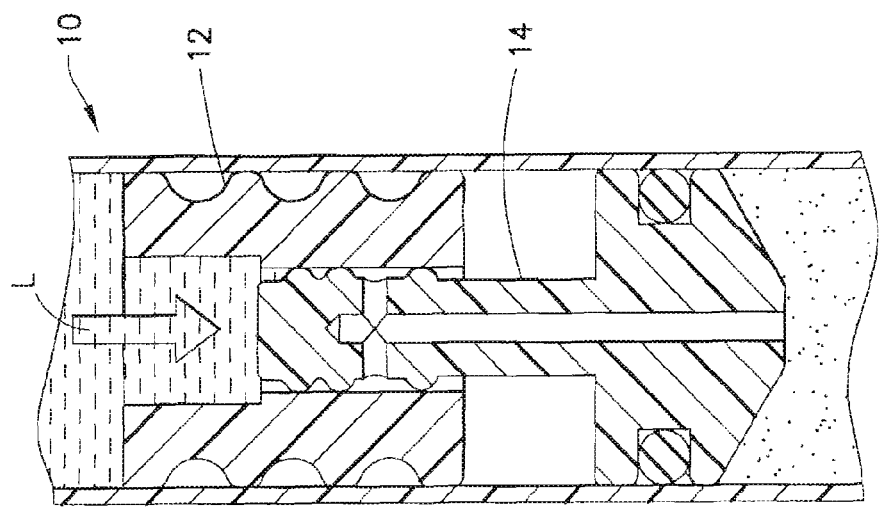

The liquid tight seal defined between the stem 38 and the channel 24 is at least partially defined between the inlet openings 44 and the distal portion 28 of the channel 24 with the poppet 14 being in the closed position as shown in FIGS. 6 and 8. A proximal sealing section 46 may be defined on the stem 38 to define this liquid tight seal with the distal portion 28 of the channel 24. With this arrangement, liquid flow from the proximal portion 26 of the channel 24 to the inlet openings 44 is prevented with the poppet 14 being in the closed position, as shown in FIGS. 6 and 8. It is further preferred that a liquid tight seal be defined between the stem 38 and the channel 24 at a location distal of the inlet openings 44 with the poppet 14 being in the open position, as shown in FIGS. 7 and 9. A distal sealing section 48 may be defined on the stem 38 to define this liquid tight seal with the distal portion 28 of the channel 24. In this manner, liquid flow from the proximal portion 26 of the channel 24 may be prevented with the poppet 14 being in the open position, thereby maximizing fluid flow through the fluid channel 34 in the poppet 14, as discussed below. The proximal and/or distal sealing sections 46, 48 may be defined by any known configuration, including by one or more of the sealing ribs 42.

The head 40 preferably engages the barrel 16 such that a greater frictional resistance against movement is generated at the interface between the head 40 and the barrel 16 than the frictional resistance against movement generated at the interface between the stem 38 and the channel 24, particularly at the interface between the stem 38 and the distal portion 28 of the channel 24. The head 40 may be formed to directly engage the barrel 16. If the poppet 14 is formed of a generally rigid material, a more compliant ring or strip 50 may be provided about the head 40 which engages the barrel 16. A pocket 51 may be defined on the head 40 shaped to seatingly receive the compliant ring 50. The compliant ring 50 may be selected so as to define a liquid tight seal with the barrel 16 to further enhance the overall sealing effect of the valve 10.

For use, the valve 10 may be placed into the barrel 16 with a dry component 52, such as a dry medicament, disposed within the barrel 16 distally of the valve 10. A wet component 54, such as a liquid, suitable for reconstituting the dry component 52 may be disposed within the barrel 16 proximally of the valve 10. With reference to FIGS. 6 and 8, the valve 10 is initially in a closed position. In the closed position, the valve 10 defines a liquid tight seal in the channel 24 such that liquid flow L (FIG. 8) through the channel 24, particularly by the liquid 54, is prevented. In addition, with the liquid tight seal defined between the body 12 and the barrel 16, liquid flow about the body 12 is also prevented. In this manner, the dry component 52 may be maintained in a dry state during storage or transportation.

Once ready for use, pressure is applied to the wet component 52 in any known manner, including through a manual or automatic application of force. With the wet component 52 being incompressible or generally incompressible, the applied pressure is transmitted to the body 12. With the frictional resistance against movement at the interface between the head 40 and the barrel 16 being greater than the frictional resistance against movement generated at the interface between the stem 38 and the channel 24, under sufficient amount of pressure, the body 12 is caused to move distally relative to the stem 38, with the poppet 14 remaining generally in a fixed position, to the open position shown in FIGS. 7 and 9. With the proximal portion 26 of the channel 24 having a larger diameter than the distal portion 28 of the channel 24, the proximal sealing section 46 comes out of engagement with the channel 24, and the inlet openings 44 are urged into communication with the proximal portion 26 of the channel 24. As such, a liquid flow path F (FIG. 9) is defined from the proximal portion 26 of the channel 24 to the outlet opening 36. It is preferred that coincident with the inlet openings 44 coming into communication with the proximal portion 26 of the channel 24, the body 12 comes into contact with the head 40. The head 40 prevents further distal movement of the body 12.

Under further application of pressure, the valve 10 remains fixed due to the frictional resistance against movement generated at the interface between the head 40 and the barrel 16, and the wet component 54 is caused to flow through the liquid flow path F to engage and mix with the dry component 52 within the barrel 16, thus, eventually causing reconstitution of the dry component 52. With reconstitution, a solution is produced ready for injection. The solution may include a pharmaceutically active agent, such as insulin.

Figure 1:
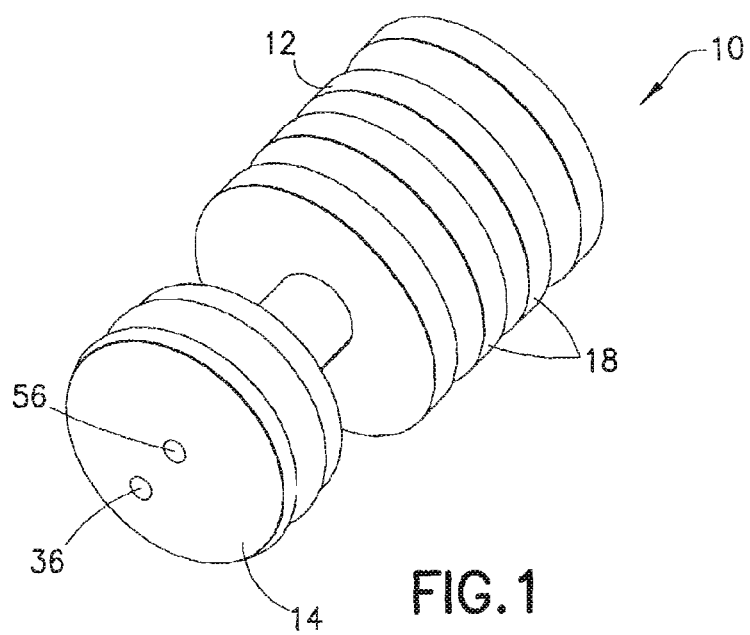
FIG. 1 is a perspective view of a valve formed in accordance with the subject invention.

With reference to FIGS. 6 and 8, it is preferred that both the body 12 and the head 40 of the poppet 14 define liquid tight seals with the barrel 16. As such, a volume of air may be entrapped between the body 12 and the head 40 which prevents, or at least provides resistance against, the movement of the body 12 from the closed (FIG. 6) to open (FIG. 7) positions. To minimize this resistance, preferably, one or more vent holes 56 is formed through the head 40, as shown in FIGS. 1, 4 and 5. The vent hole(s) 56 allow any entrapped air to vent through the head 40 as the body 12 moves distally from the closed to the open positions.

The valve 10 may be used in similar manner to mix one or more wet components, e.g., wet components being located on both sides of the valve 10. A series of the valves 10 may also be used to allow for mixing of a plurality of wet and/or dry components.

What is claimed is:
1. A drug containing device comprising:
a barrel;
a valve disposed in said barrel, said valve including:
   a body configured for slideable liquid tight engagement with said barrel, said body having a proximal end, a distal end, and a channel extending therebetween, said channel having a proximal portion and a distal portion; and,
   a poppet sealingly and slidably disposed in said channel to selectively move between first and second positions relative to said body, said poppet having a proximal end, a distal end, and a fluid channel, said fluid chan- nel defined in said poppet and extending from an outlet opening located distally of said distal end of said body;

wherein, a first portion of said poppet is in engagement with said barrel, a second portion of said poppet is in engagement with said channel, the frictional resistance against movement generated at the interface between said first portion of said poppet and said barrel being greater than the frictional resistance against movement generated at the interface between said second portion of said poppet and said channel; and, wherein, with said poppet in said first position, said poppet defining a liquid tight seal in said channel such that liquid flow through said channel is prevented, and, wherein, with said poppet in said second position, said fluid channel being in open communication with said proximal portion of said channel so as to define a liquid flow path from said proximal portion of said channel to said outlet opening.

2. A device as in claim 1, wherein said proximal portion of said channel has a larger diameter than said distal portion of said channel.

3. A device as in claim 2, wherein said poppet defines said liquid tight seal in said distal portion of said channel.

4. A device as in claim 1, wherein said poppet includes a stem and a head, said stem defining said proximal end of said poppet and said head defining said distal end of said poppet.

5. A device as in claim 4, wherein said fluid channel extends to at least one inlet opening defined on said stem, said inlet opening being spaced from said proximal end of said stem.

6. A device as in claim 4, wherein said outlet opening is defined on said head.

7. A device as in claim 4, wherein said head is located distally of said distal end of said body.

8. A device as in claim 4, wherein said first portion of said poppet is defined on said head and said second portion of said poppet is defined on said stem.

9. A device as in claim 1, wherein said device is an injector.

10. A device as in claim 1, wherein said device is a drug cartridge.

11. An assembly comprising:
a device as set forth in claim 1;
a dry component disposed within said barrel distally of said valve; and,
a liquid component for reconstituting said dry component disposed within said barrel proximally of said valve.

12. An assembly as in claim 11, wherein said device is an injector.

13. An assembly as in claim 11, wherein said device is a drug cartridge.

* * * * *